United States Patent [19]

Jakway et al.

[11] Patent Number: 5,192,657

[45] Date of Patent: Mar. 9, 1993

[54] STABILIZED PROTEOLYTIC SOLUTION AND REAGENT KIT

[75] Inventors: Janice Jakway, Bridgewater; Dennis Mochnal, Clinton, both of N.J.

[73] Assignee: Ortho Diagnostic Systems, Inc., Raritan, N.J.

[21] Appl. No.: 629,307

[22] Filed: Dec. 18, 1990

[51] Int. Cl.$^5$ .............................................. C12Q 1/00
[52] U.S. Cl. .......................................... 435/4; 435/7.2; 435/7.25; 435/810; 435/23; 435/212; 435/188
[58] Field of Search ..................... 435/7.2, 7.25, 810, 435/188, 4, 23, 212

[56] References Cited

U.S. PATENT DOCUMENTS

| | | | |
|---|---|---|---|
| 4,275,053 | 6/1981 | Rosenfield et al. | 424/12 |
| 4,403,037 | 9/1983 | Coates | 435/29 |
| 4,608,246 | 8/1986 | Bayer et al. | 435/7 |

FOREIGN PATENT DOCUMENTS

| | | |
|---|---|---|
| 252426 | 4/1961 | Australia . |
| 302754 | 8/1989 | European Pat. Off. . |
| 2919622 | of 1979 | Fed. Rep. of Germany . |
| 46-37866 | 11/1971 | Japan . |
| 47-35192 | of 1972 | Japan . |
| 57-68788 | 10/1980 | Japan . |
| 59-14788 | 7/1982 | Japan . |
| 61-15685 | of 1984 | Japan . |
| 86-04610 | 8/1986 | World Int. Prop. O. . |
| 90-05182 | 5/1990 | World Int. Prop. O. . |

OTHER PUBLICATIONS

S. D. Rolih, Journal of Blood Group Serology and Education, vol. 2, No. 6 1986, by The American Red Cross, pp. 1 and 106–110.

Leiner and Friedenson, Methods in Enzymology, vol. XIX, Proteolytic Enzymes, 1970, pp. 260–273.

Klibanov, Biochemical Society Transactions, 600th Meeting, Oxford, vol. 11, pp. 19–21.

Branch and Petz, American Society of Clinical Pathologists, Aug. 1982, vol. 78, No. 2, pp. 161–167.

Primary Examiner—Johnnie R. Brown
Assistant Examiner—Pamela S. Webber
Attorney, Agent, or Firm—Gale F. Matthews

[57] ABSTRACT

A stabilized proteolytic solution has been developed which can be used to treat selected cells, especially red blood cells. A preferred stabilized solution of the invention comprises about 0.1% to about 0.3% ficin in a citrate-buffered saline solution containing mannitol, L-cysteine, dithiothrietol in an active concentration of less than about 10 mM, and EDTA. A kit for qualitatively identifying unexpected blood group antibodies comprising a series of untreated and ficin-treated red blood cells, a stabilized ficin reagent, a red blood cell diluent and an enzyme control is also provided.

20 Claims, 2 Drawing Sheets

FIG-1

| CELL NO. | GENO- TYPE | DONOR NUMBER | Rh-hr | | | | | | | | Kell | | | | | | | Duffy | | Kidd | | Sex Linked | Lewis | | MNS | | | | P | Lutheran | | Special Antigen Typing | Cell No. | Test Results |
|---|---|---|---|---|---|---|---|---|---|---|---|---|---|---|---|---|---|---|---|---|---|---|---|---|---|---|---|---|---|---|---|---|---|
| | | | D | C | E | c | e | f | $C^w$ | V | K | k | $Kp^a$ | $Kp^b$ | $Js^a$ | $Js^b$ | $Fy^a$ | $Fy^b$ | $Jk^a$ | $Jk^b$ | $Xg^a$ | $Le^a$ | $Le^b$ | S | s | M | N | $P_1$ | $Lu^a$ | $Lu^b$ | | | |
| 1 | $R_1^wR_1$ | 11182 | + | + | 0 | 0 | + | 0 | + | 0 | + | + | 0 | + | 0 | + | 0 | + | + | 0 | + | 0 | + | 0 | + | + | + | +$^s$ | 0 | + | | 1 | |
| 2 | $R_1R_1$ | 23527 | + | + | 0 | 0 | + | 0 | 0 | 0 | 0 | + | 0 | + | 0 | + | + | + | + | 0 | + | 0 | + | + | 0 | 0 | + | 0 | 0 | + | | 2 | |
| 3 | $R_2R_2$ | 42138 | + | 0 | + | + | 0 | 0 | 0 | 0 | 0 | + | 0 | + | 0 | + | 0 | + | 0 | + | + | 0 | 0 | + | 0 | 0 | + | 0 | 0 | + | | 3 | |
| 4 | $R_0r$ | 91359 | + | 0 | 0 | + | + | + | 0 | 0 | 0 | + | 0 | + | 0 | + | 0 | + | + | + | + | 0 | + | 0 | + | + | 0 | +$^s$ | 0 | + | | 4 | |
| 5 | r'r | 61331 | 0 | + | 0 | + | + | + | 0 | 0 | 0 | + | 0 | + | 0 | + | + | + | + | 0 | + | 0 | + | 0 | + | + | + | + | 0 | + | | 5 | |
| 6 | r''r | 71284 | 0 | 0 | + | + | + | + | 0 | 0 | 0 | + | 0 | + | 0 | + | 0 | 0 | + | + | + | 0 | 0 | + | + | + | + | + | 0 | + | | 6 | |
| 7 | rr | 82564 | 0 | 0 | 0 | + | + | + | 0 | 0 | 0 | + | 0 | + | 0 | + | + | + | + | 0 | + | 0 | 0 | + | + | + | + | + | 0 | + | | 7 | |
| 8 | rr | 83178 | 0 | 0 | 0 | + | + | + | 0 | 0 | + | + | 0 | + | 0 | + | 0 | 0 | + | + | + | 0 | + | + | 0 | + | 0 | 0 | 0 | + | | 8 | |
| 9 | rr | 82045 | 0 | 0 | 0 | + | + | + | 0 | 0 | 0 | + | 0 | + | 0 | + | + | + | 0 | + | + | + | 0 | + | + | + | + | + | 0 | + | | 9 | |
| 10 | rr | 82102 | 0 | 0 | 0 | + | + | + | 0 | 0 | 0 | + | 0 | + | 0 | + | + | 0 | + | + | + | 0 | 0 | + | + | + | 0 | 0 | 0 | + | Di(a+b+) | 10 | |
| 11 | $R_2R_1$ | 91663 | + | + | + | + | + | 0 | 0 | 0 | 0 | + | 0 | + | 0 | + | + | + | + | 0 | + | 0 | + | + | + | + | + | + | 0 | + | | 11 | |

| PATIENT CELLS | | | | | | | | | | | | | | | | | | | | | | | | | | | | | | | | | |
| MODE OF REACTIVITY | | | 37°C/ANTIGLOBULIN | | | | | | | | ANTIGLOBULIN | | | | | | | VARIABLE | | VARIABLE | | | COLD | | | | VAR. | | | | | | |

| ADDITIONAL CELLS | | | Rh-hr | | | | | | | | Kell | | | | | | | Duffy | | Kidd | | Sex Linked | Lewis | | MNS | | | | P | Lutheran | | Special Antigen Typing | Cell No. | Test Results |
|---|---|---|---|---|---|---|---|---|---|---|---|---|---|---|---|---|---|---|---|---|---|---|---|---|---|---|---|---|---|---|---|---|---|
| CELL NO. | GENO- TYPE | DONOR NUMBER | D | C | E | c | e | f | $C^w$ | V | K | k | $Kp^a$ | $Kp^b$ | $Js^a$ | $Js^b$ | $Fy^a$ | $Fy^b$ | $Jk^a$ | $Jk^b$ | $Xg^a$ | $Le^a$ | $Le^b$ | S | s | M | N | $P_1$ | $Lu^a$ | $Lu^b$ | | | |

FIG-2a

| CELL NO. | GENO-TYPE | DONOR NUMBER | Rh-hr |  |  |  |  |  |  |  | KELL |  |  |  |  |  |  | DUFFY |  | KIDD |  | SEX LINKED |  | LEWIS |  | MNS |  |  |  |  | P | LUTHERAN |  | SPECIAL ANTIGEN TYPING | CELL NO. | TEST RESULTS |
|---|---|---|---|---|---|---|---|---|---|---|---|---|---|---|---|---|---|---|---|---|---|---|---|---|---|---|---|---|---|---|---|---|---|---|---|
|  |  |  | D | C | E | c | e | f | $C^w$ | V | K | k | $Kp^a$ | $Kp^b$ | $Js^a$ | $Js^b$ | $Fy^a$ | $Fy^b$ | $Jk^a$ | $Jk^b$ | $Xg^a$ | | $Le^a$ | $Le^b$ | S | s | M | N | $P_1$ | $Lu^a$ | $Lu^b$ | | | |
| 1 | $R_1R_1$ | 23673 | + | + | 0 | 0 | + | 0 | 0 | 0 | 0 | + | 0 | + | 0 | + | + | 0 | + | + | + | 0 | + | + | 0 | + | 0 | + | 0 | + | | | 1 | |
| 2 | $R_2R_2$ | 42365 | + | 0 | + | + | 0 | 0 | 0 | 0 | 0 | + | 0 | + | 0 | + | 0 | + | + | 0 | + | + | 0 | + | 0 | + | + | + | 0 | + | | | 2 | |
| 3 | rr | 83397 | 0 | 0 | 0 | + | + | + | 0 | 0 | + | + | 0 | + | 0 | + | + | + | + | + | + | 0 | + | 0 | + | + | + | + | 0 | + | | | 3 | |
| PATIENT CELLS | | | | | | | | | | | | | | | | | | | | | | | | | | | | | | | | | | | |

FIG-2b

| CELL NO. | GENO-TYPE | DONOR NUMBER | Rh-hr |  |  |  |  |  |  |  | KELL |  |  |  |  |  |  | DUFFY |  | KIDD |  | SEX LINKED |  | LEWIS |  | MNS |  |  |  |  | P | LUTHERAN |  | SPECIAL ANTIGEN TYPING | CELL NO. | TEST RESULTS |
|---|---|---|---|---|---|---|---|---|---|---|---|---|---|---|---|---|---|---|---|---|---|---|---|---|---|---|---|---|---|---|---|---|---|---|---|
|  |  |  | D | C | E | c | e | f | $C^w$ | V | K | k | $Kp^a$ | $Kp^b$ | $Js^a$ | $Js^b$ | $Fy^a$ | $Fy^b$ | $Jk^a$ | $Jk^b$ | $Xg^a$ | | $Le^a$ | $Le^b$ | S | s | M | N | $P_1$ | $Lu^a$ | $Lu^b$ | | | |
| 1 | $R_1R_1$ | 22306 | + | + | 0 | 0 | + | 0 | 0 | 0 | 0 | + | 0 | + | 0 | + | + | 0 | + | + | + | 0 | + | 0 | + | + | + | 0 | + | 0 | + | Co(a+b+) | 1 | |
| 2 | $R_2R_2$ | 52268 | + | 0 | + | + | 0 | 0 | 0 | 0 | 0 | + | 0 | + | 0 | + | 0 | + | + | 0 | + | 0 | 0 | 0 | + | + | + | +$^s$ | 0 | + | | 2 | |
| PATIENT CELLS | | | | | | | | | | | | | | | | | | | | | | | | | | | | | | | | | | | |

STABILIZED PROTEOLYTIC SOLUTION AND REAGENT KIT

BACKGROUND OF THE INVENTION

Blood group serology requires the determination of blood cell compatibility between donor and patient before a transfusion or organ transplant. Blood cell compatibility is determined by the non-occurrence of an immunological reaction between antibodies contained in the blood serum of a patient and antigens present on blood cells from a donor. A patient whose red blood cells are group A, i.e. having "A" antigens on the red cells, will have Anti-B antibodies in his or her serum. Thus, if such a person is given type B blood, an immunological reaction will occur with possible serious clinical consequences.

Tests for blood cell typing and compatibility are generally of two types: (1) agglutination tests which determine whether a specific antibody added to the cells will cause their agglutination, and (2) cell lysis tests which determine whether a specific antibody added to the tested cells together with serum complement results in hemolysis.

In blood cell typing and compatibility test procedures commonly used, both agglutination and cell lysis tests are carried out either manually by a trained technician or using automated devices. However, these tests are occassionally not sensitive enough to detect some weakly reacting antibodies or to differentiate complex mixtures of antibodies.

Enzymes are catalytic proteins which accelerate certain biological reactions. In immunohematology, proteolytic enzymes such as ficin, bromelin, papain, and trypsin remove proteins from the red cell surface. Red cell agglutination may be observed after enzyme treatment due to the greater exposure of antigen sites and/or the reduced surface charge of the red cells. This may result in a decreased cell-cell repulsion, or, enhanced antibody uptake. Certain other antigen-antibody reactions may be depressed or eliminated, due to the removal of some antigen sites after this enzyme treatment.

Enzymes can be used in two different ways in blood group serology. An enzyme solution can be added directly to a serum-cell mixture (one stage method), or the red cells can be pretreated with enzyme before serum is added (two stage method). The one stage method is faster and more convenient, but is not as sensitive as the two stage method. An advantage of the latter is better modification of the red cell membrane due to the absence of serum proteins.

When an unexpected blood group antibody is detected in a patient or donor serum, it is important to determine its specificity. The use of enzyme treated cells can be of help in determining the identity and clinical significance of the antibody. This is especially true when there are multiple specificities or the antibody has weak reactivity. Enzyme techniques strengthen the reactions seen with many blood group antibodies, especially those in the Rh and Kidd systems. Antigens in the MNS and Duffy systems are usually destroyed, so reactivity of antibodies directed against these antigens will be depressed. Standard enzyme modification techniques are described in the American Association of Blood Banks 1985, Technical Manual, 9th Ed., Arlington, VA, pp. 560-587.

One example of a diagnostic application of enzyme-treated cells is set forth in U.S. Pat. No. 4,275,053 (Rosenfield et al.). This patent discloses a solid-phase blood typing procedure based upon either agglutination or immune lysis. In this invention, a monolayer of cells is irreversibly bound to a solid matrix. A serum containing antibodies is brought into contact with the bound cell layer. Immuno-adsorption of antibodies by the bound cells occurs where the antigens of the cell membranes and the antibodies in the serum are complementary to each other. The antibody-sensitized monolayer of blood cells can either bind a second layer of blood cells carrying complementary antigen (solid-phase agglutination) or undergo lysis in the presence of serum lytic complement (solid-phase immune lysis). The results are evaluated quantitatively by such standard procedures as densitometric scanning or radioisotopic counting. It is taught at col. 12, lines 9-27 that the cells used in the Rosenfield et al. invention may be treated. For example, erythrocytes (red blood cells) may be treated with agents which potentiate agglutination such as colloids, proteases, polyelectrolytes, and buffer systems. The use of bromelin, a protease is disclosed. It is noted at col. 12, lines 35-41, that protease treatment may destroy the antigen to be assayed and "a very light treatment" is therefore taught.

Another example may be found in U.S. Pat. No. 4,608,246 (Bayer et al.). This patent discloses a method of testing the ABO forward blood grouping wherein a known antibody is attached directly to a solid surface and an unknown blood sample is activated by treating the sample with an effective quantity of a proteolytic enzyme. The activated sample is then contacted to the solid surface and any antigens specific for the known antibody will undergo immune reaction with the resulting adhered red color on the surface providing an indication of the presence of specific antigens. The invention also contemplates a method of testing applicable to reverse or serum ABO blood grouping. A solid surface capable of supporting an immunological reaction is provided and known antigens are adsorbed on the surface. The surface is then contacted with an unknown blood component which may contain unknown antibodies specific for the known antigen previously attached, in which case an immune reaction will occur. A solution of red blood cells containing the known antigen first attached to the solid surface is then activated by treating it with an effective quantity of a proteolytic enzyme. This known, activated solution is then brought into contact with the solid surface and the known antigens will undergo an immune reaction to the extent antibodies specific thereto were present in the blood component. Any resulting immunologically adhered red color on the surface will indicate the presence of these specific antibodies in the blood component. In carrying out the method of the Bayer et al. invention, it was found that considerable advantages resulted when the blood component is activated with a proteolytic enzyme which is characterized by the ability to modify red blood cells to enhance their serological activity. Examples of suitable proteolytic enzymes for this purpose include bromelin, papain, trypsin, ficin, proteinase K and pronase. A one step bromelin method is preferred.

SUMMARY OF THE INVENTION

The present invention is directed to a reagent product which comprises a stabilized proteolytic enzyme solution to remove protein from cells, especially cellular components of blood. The reagent kit as provided herein, containing the stabilized enzyme solution, is designed to aid in the selection of compatible blood for patient transfusion. Some patients requiring transfusions are incompatible with many blood units, due to rare or low levels of serum antibodies.

Kit components of the invention comprise:
i) two panels of red cells (companions), only one panel of which is treated with ficin;
ii) stabilized ficin solution;
iii) a lectin reagent (preferably a soybean derivative) used as a control to confirm that the stabilized ficin has properly treated the cellular components; and
iv) a red cell compatible buffered resuspension solution.

BRIEF DESCRIPTION OF THE DRAWINGS

FIG. 1 is an "Antigen Profile" provided with Resolve TM Panel C Ficin Treated - Resolve Panel C Untreated Antigram TM (available from Ortho Diagnostic Systems Inc.) which shows selected antigens of clinical significance depicted in tabular format useful for identification of the specificity of atypical antibodies, and recording and analyzing the results of testing performed with the kit components of the present invention. Differentiation of the antigen complexities may also be determined with the use of such a profile.

FIGS. 2a and 2b are also "Antigen Profiles" from Surgiscreen TM and Selectogen TM, respectively (each available from Ortho Diagnostic Systems Inc.). These two Antigram TM Antigen Profiles depict selected antigens useful in the screening of blood for atypical antibodies that may be present in a patient's or donor serum.

DETAILED DESCRIPTION OF THE INVENTION

One of the preferred uses of the stabilized proteolytic enzyme solution of the invention, either by itself or in the context of the kit of the invention, is in the area of immunohematology. For example, when an unexpected antibody has been detected in serum it should be identified to determine its clinical significance. In some instances, such as in the case of multiple antibody specificities or weak reactivities, it may be necessary to employ further test methods to recognize the antibody specificity(ies). The use of enzyme-treated red cells is one of the primary means by which such secondary antibody differentiation and recognition can be accomplished.

Proteolytic enzymes such as ficin modify red cell antigens in ways that enhance the reactivity of some antigen/antibody reactions and destroy or alter antigenic determinants of others. For example, following enzyme treatment of red cells, some antigens are destroyed or altered such as, but not limited to, M, N, $Fy^a$, $Fy^b$, S, $\bar{s}$, $Xg^a$, Pr, $Ch^a$, $Rg^a$ and $Yk^a$. Thus, the reactivity of antibodies directed against these antigens will be eliminated or reduced.

Alternatively, enzyme modification of red blood cells can increase the reactivity of some antibodies with their corresponding antigens, such as Rh, Kidd, Lewis, Vel and I. The exact mechanism by which antibody enhancement occurs is unknown. However, it has been suggested that the mechanism may involve either exposure of latent antigen sites on the red cell surface or that the removal of peptide chains reduces the net negative charge of the red cell, allowing agglutination to occur.

In a preferred reagent kit embodiment as provided herein, both untreated and ficin-treated cells from the same red cell donors are provided. Serological studies performed with ficin-treated red cells for the identification of blood group antibodies are considered adjunct tests and are not used as the sole means of antibody identification, because ficin destroys some clinically significant antigens. Accordingly, testing with ficin-treated red cells would normally be performed concurrently or subsequent to testing with the untreated cells.

Thus, in the preferred reagent kit embodiment, a series of untreated and ficin-treated red blood cells is provided from multiple blood donors, preferably group O (blood type) individuals, preferably ranging from about two individuals for broadbase bloodscreening utilities to about twenty individuals in the more complex antigen profile identification panels such as those shown in FIGS. 2a and 2b and FIG. 1, respectively. The individual cells are often selected to include most of the blood group factors of clinical significance. One or more of the red blood cells provided in the reagent kit invention may have been held in frozen storage, which facilitates access to rare antigen types and also to change or complete complex antigen profiles such as that depicted in FIG. 1, or smaller profiles such as those commonly used in bloodscreening, depicted in FIGS. 2a and 2b.

The untreated and treated cells are suspended in a buffered cell compatible solution. This solution generally ranges from a simple physiological saline to a preferred "cell resuspension solution". Examples of the latter are phosphate citrate buffered solutions, to which may be added a purine, a steroid and nucleosides, singly or in any combination. The latter components may be added in an amount sufficient to maintain reactivity and/or retard hemolysis of the cells during the expiration dating period. Various antimicrobial agents are generally included, such as chloramphenicol, neomycin sulfate and gentamicin to retard bacterial contamination.

The reagent kit of the invention further comprises a stabilized proteolytic enzyme solution to remove proteins from cells, which in this context are red blood cells. Although it is generally accepted that proteolytic enzymes may function in this last-mentioned capacity, enzyme solutions for this purpose are relatively unstable and deteriorate rapidly if not frozen or preserved in a more concentrated form with various stabilizing agents. The prolonged activity of enzyme solutions depends on many different interrelated factors including pH, temperature, time, concentration, activators, and stabilizers. Hence, the proteolytic enzyme solution of the present invention was designed to enhance stability and improve sensitivity.

In its broadest aspect, the stabilized proteolytic enzyme solution of the invention comprises an enzyme, a sugar, a sulphydryl compound, and a reducing agent. To better ensure that the enzyme is protected from interfering substances such as metals, often encountered in the preparation of solutions, a chelating agent is preferably included.

Enzymes useful in the stabilized proteolytic solution of the invention include those that adequately remove all or a portion of a protein, such as glycoproteins, existing on a cellular surface, such as a red blood cell surface. Of these may be mentioned as examples, ficin, bromelin, papain, chymotrypsin, trypsin, and the like.

Particularly preferred for purposes herein are ficin, papain, and bromelin, and especially ficin.

To improve stability and decrease oxidation, the pH of the stabilized proteolytic solution is generally kept under about 6.5 and preferably in a range of about 6.0 to 6.3. To control the pH of the stabilized solution, various biologic buffers may be used as diluents.

Preferred are aqueous medium such as phosphate buffered saline and citrate buffered saline solutions. Suitable concentrations of the proteolytic enzyme in the biological buffer generally range under about 1.0%, with more preferred concentrations ranging from about 0.1% to about 0.6%, and most preferably about 0.1% to about 0.3%. A concentration of 0.1% to about 0.2% may be particularly preferred, in some cases, to modify a red cell membrane without causing non-specific reactions with fresh normal human serum.

Suitable sugars for inclusion in the stabilized solution of the invention are those that help to protect the conformational structure of an enzyme, such as branched sugars, alcohol sugars, and simple sugars, examples of which are trehalose, mannitol, and sucrose, respectively. The sugar component of the formulation may also serve to reduce non-specificity of enzyme-treated cells when tested with patients, serum. In other words, non-specific aggregation caused by changes on the cell surface may be prevented, to more accurately detect immunological agglutination. Useful amounts are generally under about 300 mM, preferred amounts ranging from about 50 mM to about 150 mM, and most preferably about 50 mM to about 100 mM.

It is also desirable to protect the activity of the proteolytic solution, by protecting the active site of the enzyme, so that it can adequately cleave in the first instance, and to accelerate this catalytic action, in the second instance. A preferred component to accomplish this end is a sulphydryl compound, with L-cysteine HCl in an amount below about 10 mM being preferred. Cysteine concentrations above about 10 mM may cause a white precipitate to form in the solution, but do not necessarily affect efficacy.

However, to maintain the aesthetics of the solution and attain any appreciable amount of storage stability, (that is for at least about a month) it is preferable to employ smaller amounts of the sulphydryl compound. Accordingly, concentrations of about 7 mM to about 4 mM are most preferred. These concentrations avoid formation of an undesirable precipitate and objectionable odors.

Heretofore, efficacious dilute enzyme solutions could not be prepared with such smaller amounts of a sulphdryl compound. Surprisingly, the stabilized enzyme solution of the present invention does efficaciously employ the more desirable lower concentration of this component by a select use of a strong reducing agent. This avoids the continual oxidation process of cysteine to cystine. The reducing agent of the stabilized solution is selected from among those that are known to be strong reducing agents, such as 2-mercaptoethanol, glutathione, dithiotreitol (DTT), and the like. Most preferred among these is DTT.

Suitable amounts of this reducing agent component are concentrations whereby the component itself or in combination with enzymes does not significantly denature certain red cell antigen sites, especially the Kell system, which one does not ordinarily wish to be destroyed in a blood cell analysis. Thus, levels of the reducing agent are preferably kept relatively low because a high concentration, in combination with a proteolytic enzyme has been known to denature Kell antigen sites. Preferred are concentrations of active reducing agent lower than about 20 mM, more preferred being less than about 10 mM, and particularly preferred being about 3 mM–5 mM.

A preferred fourth component of the stabilized solution of the invention is also useful in preserving the activity of the enzyme by binding contaminant substances, accelerating enzyme activity, and preserving the microbial integrity of the solution. Thus, this component, in conjunction with commonly used preservatives such as sodium azide, facilitates the packaging of the solution, as this packaging may be under non-sterile conditions. Accordingly, preferred embodiments of the solution of the invention comprise a chelating agent, such as ethylenediaminetetraacetic acid (EDTA), ethylenebis-(oxyethylene nitrilo)-tetraacetic acid (EGTA), and the like. Amounts useful in the stabilized solution are amounts that will not interfere with buffering of the formulation, or inactivate the system in some way. Preferred amounts are less than about 4 mM, and more preferably between about 1 mM to about 2 mM.

The reagent kit of the invention preferably includes an enzyme control. Such a control demonstrates that the stabilized ficin solution has retained its activity and that the procedures for carrying out the steps of the assay utilizing the reagent kit and its stabilized enzyme solution have been followed. This control reacts with exposed sites after enzyme treatment. It thus causes agglutination with properly treated cells, while untreated cells do not agglutinate. Any suitable control known to the art for this purpose may be usefully employed in the kit of the invention. However, particularly suitable are glycoprotein extracts (lectins) from soybean plants such as Glycine soja. Suitable dilutions of the soybean lectin may be routinely optimized for use with enzyme-treated cells, taken into consideration polyagglutinable cell reactivities, such as those seen in certain disease states.

In accordance with the method of testing as provided herein, patient serum may be tested to resolve unexpected antibody complexities in the sense of screening for or more specific identification of such atypical antibodies. Thus, a sample of a patient's plasma or serum is combined with both the ficin-treated and untreated donor cells. This mixture is then examined for the presence or absence of agglutination and/or hemolysis after an incubation phase of testing and in an antiglobulin phase of testing. Agglutination and/or hemolysis constitutes a positive test, and the absence of either is considered a negative test providing the antigen to which the antibody is directed is present and the antibody is at a concentration which allows detection. The results for each test phase may be recorded. Identification of the antibody present in the serum may be made by matching the reactions obtained with those established on an Antigen Profile, such as that depicted in FIGS. 2a and 2b for screening purposes, or FIG. 1 for specific identification purposes.

The following specificities are examples of antibodies which may be enhanced when testing is performed with ficin-treated red cells: Anti—D, —C, —E, —c, —e, —f, —JK$^a$, —JK$^b$, —Le$^a$, —Le$^b$, —P$_1$, —I, —IH, —Vel, —PP$_1$P$^k$ and —P.

The following specificities are examples of antibodies whose reactivity may be eliminated or reduced when testing is performed with ficin-treated red cells: Anti- —Fy$^a$, —Fy$^b$, —S, —e,ovs/s/, —M, —N, —Xg$^a$, —Pr, —Ch$^a$, —Rg$^a$ and —Yk$^a$.

A ficin-treated auto control, i.e., a test of the individual's serum with his own ficin-treated red cells, is preferably performed with every panel and carried through the same test phases.

The invention is further illustrated by means of the following examples. These examples are meant to be illustrations only and are not intended to limit the present invention to the specific embodiments.

EXAMPLE 1

A stabilized ficin solution was prepared, which comprised ficin, dithiothreitol (DTT), and L-cysteine in an acidic medium of about pH 6.0 to about 6.3. The maximum concentration of DTT was below about 10 mM.

In another example, the ficin solution contained Mannitol (about 18.2 g/L), citric acid (about 0.168 g/L), DTT (about 0.62 g/L), EDTA (about 0.372 g/L), sodium azide (about 1.0 g/L), sodium chloride (about 9.0 g/L), sodium citrate (about 2.71 g/L) and L-cysteine hydrochloride (L-cysteine HCl) (about 0.88 g/L).

To ensure maximum reactivity and consistency of the stabilized ficin solution, a quantified stock ficin solution is first prepared by dissolving ficin powder into a buffered phosphate solution. Desired quantities of the remaining materials as referred to above are then added to distilled or deionized water to prepare a diluent. These latter components are added in a sequence that maintains optimal activity of the components in accordance with accepted techniques. In order to retain optimal enzyme activity, the stock ficin solution must be added to the diluent within a relatively short time period, such as within 24 hours. Approximately 20% of the stock ficin solution is added to the diluent, which is then filtered and placed into suitable containers. The result is a stabilized ficin solution, even at elevated temperatures such as 25° C., and even when exposed to air.

EXAMPLE 2—
A TEST METHOD

Twelve small test tubes are labelled and placed in a rack. The 12th tube is included as an autologous control. To each tube, two drops of the serum under test are added with, a Pasteur pipette. One drop of ficin treated cell reagent is added to tubes #1-11. To the auto control tube, one drop of ficin-treated patient's cells is added. The tubes are mixed well and incubated at 37° C. for 15 to 30 minutes. The tubes are centrifuged for approximately 15 seconds at 3400 rpm (900–1000 rcf) or 1 minute at 100 rpm (100–125 rcf). The cells in all test tubes are resuspended by gentle agitation and examined macroscopically for hemolysis and/or agglutination. An optical aid, such as a hand lens or magnifying mirror, may enhance visibility of weak reactions. Complete hemolysis precludes further testing and is interpreted as a positive result. If partial hemolysis or agglutination occurs, the cells in each tube are washed at least three times with tubes full of isotonic saline. The saline is decanted and drained completely after the last wash. Two drops of Bioclone Anti-Human Globulin™ obtained from Ortho Diagnostic Systems Inc. or an appropriate amount of another anti-human globulin are added to each tube. The contents of each tube are mixed well and centrifuged, as described above. The cells are resuspended and promptly examined macroscopically for agglutination. All negative antiglobulin tests should be controlled by adding red blood cells sensitized with IgG antibody (e g. ORTHO Coombs Control™, which may be obtained from Ortho Diagnostic Systems Inc.).

EXAMPLE 3

AUTO CONTROL PREPARATION

Patient red cells are washed at least three times in isotonic saline. One drop of stabilized ficin solution is added to a test tube. One drop of washed packed cells is added and incubated for 15 minutes at 37° C. The cells are then washed three times with isotonic saline which is decanted completely after the last wash. The cells are resuspended with a reagent red blood cell diluent to an approximate 3% cell suspension. The treated cells are then tested for adequate enzyme treatment by comparing patient and ficin treated cells added to an enzyme control solution which is a dilution of the soybean lectin *Glycine max.* (*G. soja*). Both tubes are centrifuged as described in Example 1. The cell buttons are suspended and observed macroscopically for agglutination.

EXAMPLE 4

Stabilized Ficin Solutions Stabilities-Reactivity Cell #772581

|  |  |  | 37° C.[1] | AGT[2] | RT[3] | IS[4] |
|---|---|---|---|---|---|---|
| 37° C. |  |  |  |  |  |  |
| 89-AS-114 | 5° C. | 1) | 3 | 0 | 0 | 3½ |
| (31 wks) 5° C. per vial |  | 2) | 3 | 0 | 0 | 4 |
| 89-AS-132 | 5° C. | 3) | 3 | 0 | 0 | 3½ |
| (28 wks) open vial | 5° C. | 4) | 1½ | 0 | 0 | 3½ |
| 89-AS-139 | 5° C. | 5) | 3 | 0 | 0 | 3 |
| (27 wks) open vial | 5° C. | 6) | 3 | 0 | 0 | 4 |
| 89-AS-166 | 5° C. | 7) | 3 | 0 | 0 | 4 |
| (23 wks) open vial | *25° C. 5° C. | 8) | 2½ | 0 | 0 | 4 |
| 89-AS-215 | 5° C. | 9) | 3 | 0 | 0 | 4 |
| (12 wks) open vial | *25° C. 5° C. | 10) | 3 | 0 | 0 | 4 |
| 89-AS-216 | 5° C. | 11) | 3 | 0 | 0 | 3½ |
| (10 wks) open vial | *25° C. 5° C. | 12) | 3 | 0 | 0 | 3½ |
| exp. 6/5/90 Gamma EN244-1 |  | 13) | 1 | 2 | 1½ | 2½ |
| untreated cell |  | 14) | 0 | 2 | 3½ | 0 |

[1] Anti-D 86-407653 - 1:500
[2] Anti-FY$^a$ - FY$^a$ 175B
[3] Anti-N - Gam NL 138-2 - obtained from Gamma Biologics Inc.
[4] Enzyme Control - 89-AS-192
Conclusion: FY$^a$N antigens destroyed, D enhanced, Enzyme Control reaction good
Key:
Number = reaction strength on a scale of 0–4.
RT = room temperature (approx. 15 min.–30 min.) all cells have been ficin-treated except for "untreated cells" which serves as control
AGT = anti-globulin test
IS = immediate spin
"37° C." = incubation temperature for about 15–30 minutes

| | Stabilities Stabilized Ficin Solutions | | | | | |
|---|---|---|---|---|---|---|
| | | | 1.[1] | 1.[2] | 1.[3] | 1.[4] |
| 89-AS-114 (55 weeks) open vial | −5° C. | 1) | 3½ | 0 | 0 | 4 |
| 89-AS-132 (52 weeks) open vial | −5° C. | 2) | 3 | 0 | 0 | 4 |
| | −5° C. | 3) | 3 | 0 | 0 | 4 |
| | −5° C. | 4) | 3 | 0 | 0 | 4 |
| 89-AS-139 (51 weeks) open vial | −5° C. | 5) | 3½ | 0 | 0 | 3½ |
| | −5° C. | 6) | 3½ | 0 | 0 | 3½ |
| 89-AS-116 | −5° C. | 7) | 3 | 0 | 0 | 4 |

| | | Stabilities Stabilized Ficin Solutions | | | |
|---|---|---|---|---|---|
| | | 1.[1] | 1.[2] | 1.[3] | 1.[4] |
| (47 weeks) | −25° C. | 8) 2½ | 2 | 1¼ | 3¼ |
| open vial | −5° C. | 9) 3½ | 0 | 0 | 3¼ |
| 89-AS-215 | −5° C. | 10) 3½ | 0 | 0 | 3¼ |
| (36 weeks) | −25° C. | 11) 3 | 0 | 0 | 3¼ |
| open vial | −5° C. | 12) 3 | 0 | 0 | 3¼ |
| 89-AS-216 | −5° C. | 13) 3 | 0 | 0 | 3¼ |
| (34 weeks) | −25° C. | 14) 2¾ | 0 | 0 | 4 |
| open vial | −5° C. | 15) 3½ | 0 | 0 | 4 |
| SFS,201 (RC102) (open vial) 4/5/90 | | 16) 2½ | 0 | 0 | 3¼ |
| SFS202 (RC106) unopened | −5° C. | 17) 3½ | 0 | 0 | 3¼ |
| Gamma EN244-1 exp. 6/5/90 | | 18) 2½ | 1 | 1 | 3¼ |
| untreated cell | | 20) 0 | 3 | 2¼ | 0 |

1.[1] - Anti-D - 1:500 - 86407653
1.[2] - Anti-Fy$^a$ - FA176A2
1.[3] - Anti-N - NM06-1
1.[4] - Enzyme Control - FEC101

Key:
Number = reaction strength on a scale of 0–4.
RT = room temperature (approx. 15 min.–30 min.) all cells have been ficin-treated except for "untreated cells" which serves as control
AGT = anti-globulin test
IS = immediate spin
"37° C." = incubation temperature for about 15–30 minutes
−25° C. vials of 89-AS-166, 215, 216 losing reactivity (between average 34–37 weeks)
−5° C. vials all stable for at least one year (3 lots) 89-AS-114, 132, 139

EXAMPLE 5

Purpose: To determine what level of DTT in Stabilized Ficin Solution will destroy or depress Kell antigens.

Materials:
1. Stabilized Ficin Solution, SFS 202, containing 4 mm DTT Want to simulate ZZAP reagent (American Assoc. of Blood Banks Tech Manual, 1990, p. 584.)
2. DTT (Research Organics Lot B3964, M.W. 154.2 per 5 ml Stab. Fic. Soln =
   1) 200 mm DTT—additional (196 mm added)—0.151 g/5ml DTT added
   2) 150 mm DTT = −0.113 g DTT/5 ml
   3) 100 mm DTT = −0.074 g DTT/5 ml
   4) 50 mm DTT = −0.035 g DTT/5 ml
   5) 20 mm DTT = −0.012 g DTT/5 ml
3. ZZAP reagent (Tech-Manual 1990, pg. 584)
   1. 0.2 m DTT (0.1 g in 3.24 ml, PBS, pH 6.2)
   2. 1% ficin (stock—stored frozen)
      ZZAP:
      1 ml 1% ficin
      2.5 ml of 0.2 m DTT
      1.5 ml of PBS Method 2 cells, ACD collected—washed × 3 1 drop cells, 1 drop Stab. Ficin Solutions 15, 37° C., wash × 3

| | Enzyme Control RC104 IS | Anti-Kell KC1330 AGT | Anti-cellano LK-41A AGT |
|---|---|---|---|
| Cell: K + k + 180237 | | | |
| 1) Stab. Ficin SFS202 (4 mM DTT − Final DTT) | 3½ | 2½ | 2 |
| 2) SFS202 + 16 mM DTT (20 mM Final DTT) | 3½ | 0 | 0 |
| 3) SFS202 + 46 mM DTT (50 mM Final DTT) | 3½ | 0 | 0 |
| 4) SFS202 + 96 mM DTT (100 mM Final DTT) | 3½ | 0 | ½ |
| 5) SFS202 + 146 mM DTT (150 mM Final DTT) | 3½ | 0 | 0 |
| 6) SFS202 + 196 mM DTT (200 mM Final DTT) | 3½ | 0 | 0 |
| 7) ZZAP − 100 mM DTT | 3½ | 0 | 0 |
| 8) Untreated cell | 0 | 2½ | 2½ |
| Cell: K − k + 182386 | | | |
| 1) SFS202 − 4 mM DTT | 3½ | (K−)NT | 3 |
| 2) SFS − 20 mM DTT | 3½ | (K−)NT | 0 |
| 3) SFS − 50 mM DTT | 3½ | (K−)NT | 0 |
| 4) SFS − 100 mM DTT | 3½ | (K−)NT | 0 |
| 5) SFS − 150 mM DTT | 3½ | (K−)NT | 0 |
| 6) SFS − 200 mM DTT | 3½ | (K−)NT | 0 |
| 7) ZZAP − 100 mM DTT | 3½ | (K−)NT | 0 |
| 8) Untreated Cell | 0 | (K−)NT | 3 |
| Control Ortho Cell - RA594 #2 K + k + untreated cell | | 2½ | 2½ |
| #1 K − k + untreated cell | | 0 | NT |
| Cell panel obtained from Immucor-21086 #14 K + k − untreated cell | | NT | 0 |

Conclusion: Kell antigens destroyed at 20 mM DTT concentration (and above) to try lower amounts between 4 mM and 20 mM DTT Key:
Number = reaction strength on a scale of 0–4.
RT = room temperature (approx. 15 min.–30 min.) all cells have been ficin-treated except for "untreated cells" which serves as control
AGT = anti-globulin test
IS = immediate spin
"37° C." = incubation temperature for about 15–30 minutes Purpose:
Test Stabilized Ficin Solutions (SFS) with DTT concentrations lower than 20 mM to determine at what point Kell antigens are depressed.

Materials:
as before, with SFS 202
1) 5 mM DTT = 0.0015g DTT added to 10ml SFS202
2) 10 mM DTT = 0.0046g DTT added to 5ml SFS 202
3) 15 mM DTT = 0.0085g DTT added to 5mL SFS 202
4) 20 mM DTT = as prepared previously (used same vial)
5) 4 mM DTT = SFS 202—not treated with additional DTT Method:
50ul 3 × washed packed cells
50ul Stabilized Ficin Solutions
15, 37° C., wash × 3 —suspend to approx. 3% in 0/9% saline

| | Enzyme Control RC104 IS | Anti-Kell KC1330 AGT | Anti-cellano LK-41A AGT |
|---|---|---|---|
| Cell: K + k + 180237 | | | |
| SFS202 (4 mM DTT Final) | 3½ | 3 | 3 |
| (5 mM DTT) | 3½ | 3 | 3 |
| (10 mM DTT) | 3½ | 1½ | ½ |
| (15 mM DTT) | 3½ | 0 | 0 |
| (20 mM DTT) | 3½ | 3 | 1 |
| untreated cell | 0 | 3 | 2½ |
| Cell: 182386 K − k + | | | |
| SFS202 (4 mM DTT) | 3½ | (K−)NT | 3 |

|  | Enzyme Control RC104 IS | Anti-Kell KC1330 AGT | Anti-cellano LK-41A AGT |
|---|---|---|---|
| (5 mM DTT) | 3¾ | (K−)NT | 3 |
| (10 mM DTT) | 3¾ | (K−)NT | 1 |
| (15 mM DTT) | 3¾ | (K−)NT | 0 |
| (20 mM DTT) | 3¾ | (K−)NT | 1½ |
| untreated cell | 0 | (K−)NT | 2½ |

Conclusion: Critical level of DTT with a freshly prepared solution is about 10 mM, if avoiding Kell antigen destruction. Oxidation or evaporation of DTT causes reduced Kell destruction with 20 mM vial previously prepared

SUMMARY
STABILIZED FICIN SOLUTION STABILITY STUDY
DEMONSTRATION OF SEROLOGICAL ENHANCEMENT WITH ANTI-D SERUM

| LOTS | STORAGE CONDITION | TIME (MONTHS) REACTION STRENGTH ON A SCALE OF 0–4 | | | |
|---|---|---|---|---|---|
| | | 1 | 3 | 6 | 12 |
| 1) LOT 89-AS-139 | A) 5 C. | 3.50 | 3.25 | 3.00 | 3.50 |
| | B) 5 C. (open vial) | 3.50 | 3.25 | 3.00 | 3.50 |
| | C) 25 C. | 3.50 | 3.25 | NT | NT |
| 2) CONTROL-UNTREATED CELLS | | 0 | 0 | 0 | 0 |
| 1) LOT 89-AS-166 | A) 5 C. | 2.50 | 3.25 | 3.00 | 2.50 |
| | B) 5 C. (open vial) | 1.50 | 3.25 | 2.50 | 2.50 |
| | C) 25 C. | 1.50 | 3.25 | NT | 0 |
| 2) CONTROL-UNTREATED CELLS | | 0 | 0 | 0 | 0 |
| 1) LOT 89-AS-215 | A) 5 C. | 2.75 | 3.00 | 3.50 | 2.00 |
| | B) 5 C. (open vial) | 3.00 | 3.00 | 3.75 | 1.50 |
| | C) 25 C. | 2.50 | NT | 3.75 | 2.25 |
| 2) CONTROL-UNTREATED CELLS | | 0 | 0 | 0 | 0 |
| 1) COMPETITOR (5 C. open vial) | | 3.00 | 2.50 | 1.00 | 2.5 |
| 2) CONTROL-UNTREATED CELLS | | 0 | 0 | 0 | 0 |

STABILIZED FICIN SOLUTION STABILITY STUDY
DEMONSTRATION OF DUFFY ANTIGEN DESTRUCTION/DEPRESSION ACTIVITY

| LOTS | STORAGE CONDITION | TIME (MONTHS) | | | |
|---|---|---|---|---|---|
| | | 1 | 3 | 6 | 12 |
| 1) LOT 89-AS-139 | 5 C. | 0 | 0 | 0 | 0 |
| | 5 C. (open vial) | 0 | 0 | 0 | 0 |
| | 25 C. | 0 | 0 | NT | NT |
| 2) CONTROL-UNTREATED CELLS | | 2.50 | 2.00 | 2.00 | 3.00 |
| 1) LOT 89-AS-166 | 5 C. | 0 | 0 | 0 | 0 |
| | 5 C. (open vial) | 0 | 0 | 0 | 0 |
| | 25 C. | 0 | 0 | NT | 3.00 |
| 2) CONTROL-UNTREATED CELLS | | 2.00 | 2.00 | 2.00 | 2.50 |
| 1) LOT 89-AS-215 | 5 C. | 0 | 0 | 0 | 0 |
| | 5 C. (open vial) | 0 | 0 | 0 | 0 |
| | 25 C. | 0 | NT | 0 | 1.00 |
| 2) CONTROL-UNTREATED CELLS | | 2.50 | 3.50 | 3.00 | 2.50 |
| 1) COMPETITOR (5 C. open vial) | | 0 | 0.25 | 2.00 | 1.00 |
| 2) CONTROL-UNTREATED CELLS | | 2.50 | 2.00 | 2.00 | 3.00 |

STABILIZED FICIN SOLUTION STABILITY STUDY
DEMONSTRATION OF ANTI-N DESTRUCTION/DEPRESSION ACTIVITY

| LOTS | STORAGE CONDITION | TIME (MONTHS) | | | |
|---|---|---|---|---|---|
| | | 1 | 3 | 6 | 12 |
| 1) LOT 89-AS-139 | 5 C. | 0 | 0 | 0 | 0 |
| | 5 C. (open vial) | 0 | 0 | 0 | 0 |
| | 25 C. | 0 | 0 | NT | NT |
| 2) CONTROL-UNTREATED CELLS | | 2.00 | 1.50 | 3.50 | 2.75 |
| 1) LOT 89-AS-166 | 5 C. | 0 | 0 | 0 | 0 |
| | 5 C. (open vial) | 0 | 0 | 0 | 0 |

STABILIZED FICIN SOLUTION STABILITY STUDY
DEMONSTRATION OF ANTI-N DESTRUCTION/DEPRESSION ACTIVITY

| LOTS | STORAGE CONDITION | 1 | 3 | 6 | 12 |
|---|---|---|---|---|---|
| | 25 C. | 0 | 0 | NT | 3.00 |
| 2) CONTROL-UNTREATED CELLS | | 3.00 | 1.50 | 3.50 | 2.50 |
| 1) LOT 89-AS-215 | 5 C. | 0 | 0 | 0 | 0 |
| | 5 C. (open vial) | 0 | 0 | 0 | 0 |
| | 25 C. | 0 | NT | 0 | 1.00 |
| 2) CONTROL-UNTREATED CELLS | | 2.00 | 3.50 | 3.75 | 2.50 |
| 1) COMPETITOR (5 C. open vial) | | 0 | 0 | 1.50 | 1.00 |
| 2) CONTROL-UNTREATED CELLS | | 2.00 | 1.50 | 3.50 | 2.75 |

What is claimed:

1. A stabilized proteolytic solution comprising ficin, L-cysteine, and dithiothreitol (DTT) in an acidic aqueous medium.

2. The solution of claim 1 wherein said acidic medium is between about pH 6.0 and about pH 6.3.

3. The solution of claim 1 wherein the concentration of active DTT does not exceed 10 mM.

4. The solution of claim 3 wherein said DTT active concentration is about 2 mM to about 4 mM.

5. The solution of claim 3 further comprising ethylenediaminetetraacetic acid (EDTA).

6. The solution of claim 1 further comprising a sugar.

7. The solution of claim 6 wherein said sugar comprises mannitol or trehalose.

8. The solution of claim 1 wherein said ficin concentration is between about 0.1% and about 0.3%.

9. The solution of claim 8 wherein said ficin concentration is about 0.2%.

10. A stable ficin solution comprising D-mannitol, citric acid, . L-cysteine, dithiothreitol (DTT), and ethylenediaminetetraacetic acid (EDTA) in an aqueous medium.

11. A kit for qualitatively identifying blood group antibodies comprising:
  a series of ficin-treated and untreated red blood cells selected to include most of the blood group factors of clinical significance suspended in red blood cell diluent;
  red blood cell diluent; and
  stable ficin solution.

12. The kit of claim 11 further comprising enzyme control solution.

13. The kit of claim 11 wherein said red blood cell diluent comprises a phosphate-citrate buffered solution to which a purine, a steroid, and nucleosides have been added.

14. The kit of claim 12 wherein said enzyme control solution comprises a buffered solution of lectin *Glycine max.* (*G. soja*).

15. The kit of claim 11 wherein said stable ficin solution comprises ficin, dithiothreitol (DTT), and L-cysteine in an acidic medium.

16. The kit of claim 15 wherein said acidic medium is between about pH 6.0 and about pH 6.3.

17. The kit of claim 15 wherein the concentration of DTT does not exceed 10 mM.

18. The kit of claim 15 wherein said stable ficin solution further comprises ethylenediaminetetraacetic acid (EDTA).

19. The kit of claim 15 wherein said stable ficin solution further comprises a sugar.

20. The kit of claim 19 wherein said sugar comprises mannitol or trehalose.